United States Patent
Sarsani et al.

(10) Patent No.: US 10,995,044 B2
(45) Date of Patent: May 4, 2021

(54) IGNITION OF OXIDATIVE COUPLING OF METHANE WHILE REDUCING RATIO OF METHANE TO OXYGEN

(71) Applicant: SABIC Global Technologies B.V., Bergen op Zoom (NL)

(72) Inventors: Sagar Sarsani, Sugar Land, TX (US); David West, Sugar Land, TX (US); Vemuri Balakotaiah, Sugar Land, TX (US); Wugeng Liang, Sugar Land, TX (US); Jonathan Banke, Sugar Land, TX (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/946,688

(22) Filed: Jul. 1, 2020

(65) Prior Publication Data
US 2020/0339488 A1     Oct. 29, 2020

Related U.S. Application Data

(62) Division of application No. 16/483,563, filed as application No. PCT/IB2018/050714 on Feb. 5, 2018, now Pat. No. 10,843,982.

(Continued)

(51) Int. Cl.
*C07C 2/84*     (2006.01)
*C07C 9/06*     (2006.01)
(Continued)

(52) U.S. Cl.
CPC ............ *C07C 2/84* (2013.01); *C07C 2/78* (2013.01); *C07C 2/82* (2013.01); *C07C 9/06* (2013.01);
(Continued)

(58) Field of Classification Search
CPC .... C07C 2/84; C07C 2/78; C07C 2/82; C07C 9/06; C07C 9/08; C07C 11/04;
(Continued)

(56) References Cited

U.S. PATENT DOCUMENTS

| | | | |
|---|---|---|---|
| 4,876,409 A | 10/1989 | Leyshon et al. | |
| 5,288,924 A | 2/1994 | Beech, Jr. et al. | |

(Continued)

FOREIGN PATENT DOCUMENTS

| | | |
|---|---|---|
| AU | 2013355038 | 11/2017 |
| SG | 146924 | 11/2008 |

OTHER PUBLICATIONS

Tarasov and Kustov; "Autothermal Methane Oxidative Coupling Process over La2O3/MgO Catalysts", Chem. Eng. Technol., 2015, 38, No. 12, 2243-2252 (Year: 2015).*

(Continued)

*Primary Examiner* — Ali Z Fadhel
(74) *Attorney, Agent, or Firm* — Norton Rose Fulbright US LLP

(57) ABSTRACT

Methods of performing a startup of an oxidative coupling of methane reaction to produce $C_2+$ hydrocarbons are described. The methods can include incrementally varying startup parameters of the oxidative methane reactor and using the feed gas as a coolant such that high $C_2+$ hydrocarbon selectivity is achieved.

8 Claims, 3 Drawing Sheets

Related U.S. Application Data

(60) Provisional application No. 62/457,119, filed on Feb. 9, 2017.

(51) Int. Cl.
| | |
|---|---|
| *C07C 9/08* | (2006.01) |
| *C07C 11/04* | (2006.01) |
| *C07C 11/06* | (2006.01) |
| *C07C 2/78* | (2006.01) |
| *C07C 2/82* | (2006.01) |
| *C07C 2/80* | (2006.01) |

(52) U.S. Cl.
CPC ............... *C07C 9/08* (2013.01); *C07C 11/04* (2013.01); *C07C 11/06* (2013.01); *C07C 2/80* (2013.01); *C07C 2521/08* (2013.01); *C07C 2523/02* (2013.01); *C07C 2523/10* (2013.01); *C07C 2523/888* (2013.01); *C07C 2523/889* (2013.01); *C10G 2300/4031* (2013.01)

(58) Field of Classification Search
CPC . C07C 11/06; C07C 2521/08; C07C 2523/02; C07C 2523/10; C07C 2523/888; C07C 2523/889; C07C 2523/04; C07C 2523/30; C07C 2523/34; C10G 2300/4031; B01J 23/34; B01J 23/02; B01J 23/10; Y02P 20/52
See application file for complete search history.

(56) References Cited

U.S. PATENT DOCUMENTS

| | | | |
|---|---|---|---|
| 5,763,722 A | 6/1998 | Vic et al. | |
| 6,087,545 A | 7/2000 | Choudhary et al. | |
| 6,726,850 B1 | 4/2004 | Reyes et al. | |
| 8,815,080 B2 | 8/2014 | Sundaram | |
| 2013/0225884 A1 | 8/2013 | Weinberger et al. | |
| 2014/0107385 A1* | 4/2014 | Schammel | B01J 8/067 585/501 |
| 2014/0128484 A1 | 5/2014 | Hassan et al. | |
| 2015/0152025 A1 | 6/2015 | Cizeron et al. | |
| 2015/0307415 A1 | 10/2015 | Rafique et al. | |
| 2015/0321974 A1 | 11/2015 | Schammel et al. | |
| 2015/0329439 A1 | 11/2015 | Nyce et al. | |

OTHER PUBLICATIONS

Hohn, et al., "Methane coupling to acetylene over Pt-coated monoliths at millisecond contact times," *Catalysis Letters*, 1998, 54:113-118.

International Search Report and Written Opinion issued in counterpart International Patent Application No. PCT/IB2018/050714, dated May 15, 2018.

Lunsford, J.H., "Catalytic conversion of methane to more useful chemicals and fuels: a challenge for the 21$^{st}$ century" *Catl. Todays*, 2000, 63:165-174.

Mleczko, et al., "Catalytic oxidative coupling of methane-reaction engineering aspects and process schemes," *Fuel Processing Technology*, 1995, 42(2-3):217-248.

Tarasov, et al., "Autothermal Methane Oxidative Coupling Process over $La_2O_3$/MgO Catalysts," *Chemical Engineering Technology*, 2015, 38(12):2243-2252.

Wang et al., "Autothermal oxidative coupling of methane on the $SrCO_3$/$Sm_2O_3$ catalysts," *Catalysis Communications*, 2009, 10:807-810.

Wang, et al., "Oxidative Coupling of Methane over Oxide-Supported Sodium-Manganese Catalysts" *J. Catal.*, 1995, 155:390-402.

Wozny, et al., "Oxidative Coupling of Methane: A Design of Integrated Catalytic processes" *Chemical Engineering*, 2010, 21:1399-1404.

* cited by examiner

IGNITION OF OXIDATIVE COUPLING OF METHANE WHILE REDUCING RATIO OF METHANE TO OXYGEN

CROSS REFERENCE TO RELATED APPLICATIONS

This application is a divisional of U.S. patent application Ser. No. 16/483,563 filed Aug. 5, 2019, which is a national phase application under 35 U.S.C. § 371 of International Application No. PCT/IB2018/050714 filed Feb. 5, 2018, which claims the benefit of priority of U.S. Provisional Patent Application No. 62/457,119 filed Feb. 9, 2017, all of which are hereby incorporated by reference in their entirety.

BACKGROUND OF THE INVENTION

A. Field of the Invention

The invention generally concerns systems and methods for the production of $C_2+$ hydrocarbons from methane ($CH_4$) and oxygen ($O_2$). In particular, the systems and methods allow for the use of parameters of reactant feed to a reactor to establish and maintain steady state operation.

B. Description of Related Art

Methane can be used to produce ethane and/or ethylene through the oxidative coupling of the methane (OCM) reaction. While extensive research and development has been devoted to this reaction, the reaction largely remains inefficient on a commercial scale. One of the key challenges is the high reaction temperature (typically greater than 750° C.) required to make the reaction proceed. The need for such a high temperature is due to the bond strength (bond dissociation energy) of the tetrahedral C—H bonds in methane, which is 104 kcal per mole (kcal/mol). This C—H bond strength makes methane less reactive and difficult to undergo oxidative conversion to form ethylene.

The oxidative coupling of the methane is represented by the following equations:

$$2CH_4 + O_2 \rightarrow C_2H_4 + 2H_2O \quad \Delta H = -67.4 \text{ kcal/mol} \quad (I)$$

$$2CH_4 + \tfrac{1}{2}O_2 \rightarrow C_2H_6 + H_2O \quad \Delta H = -84.6 \text{ kcal/mol} \quad (II)$$

As shown in Equations (I) and (II), oxidative conversion of methane to ethylene or ethane is exothermic. It should be noted that the heats of reaction for Equations (I) to (IV) are given per 100593174.1 mole of oxygen consumed. Excess heat produced from these reactions can push conversion of methane to carbon monoxide and carbon dioxide rather than the desired $C_2$ hydrocarbon product:

$$CH_4 + 1.5 O_2 \rightarrow CO + 2H_2O \quad \Delta H = -82.8 \text{ kcal/mol} \quad (III)$$

$$CH_4 + 2 O_2 \rightarrow CO_2 + 2H_2O \quad \Delta H = -95.9 \text{ kcal/mol} \quad (IV)$$

The excess heat from the reactions in Equations (III) and (IV) further exacerbate this situation, thereby substantially reducing the selectivity of ethylene production when compared with carbon monoxide and carbon dioxide production.

Equations (V) through (VIII) provide an illustration of the chemical pathway in which the OCM reaction can occur in the presence of a catalyst:

$$O_2 + 2[*] \rightarrow 2[O], \quad (V)$$

$$CH_4 + [O] \rightarrow CH_3 + [OH] \quad (VI)$$

$$2CH_3 \rightarrow C_2H_6 \rightarrow C_2H_4 \rightarrow CO_x \quad (VII)$$

$$2[OH] \rightarrow [O] + [*] + H_2O \quad (VIII)$$

where * is a vacant catalytic surface site. The coupling of methyl radicals in equation (VII) occurs in the gas phase while the formation of $C_2H_4$ and $CO_x$ may either be catalytic or in the gas phase. The remaining reactions (V, VI, and VIII) occur on the catalyst.

There are two important practical problems that have prevented the development of a commercially feasible OCM process: (1) the very large heat of reaction (Equations I-IV); and (2) the very high temperature required to initiate the reaction (typically 700-950° C.). There is no commercially available liquid heat transfer fluid capable of operation at such high temperature. Consequently, the only way to cool a reactor at this range of temperature is with very inefficient gas phase coolants (air, steam, or ethane, for example). In a cooled multi-tubular fixed bed reactor, the methane conversion must be limited (by the oxygen concentration in the feed) to less than about 15% in order to avoid a runaway reaction. A runaway reaction is one in which the temperature rise within the catalyst bed is high enough to damage or deactivate the catalyst.

Attempts have been made to address the problem of temperature control by using one or more substantially adiabatic reactors in series with one or more heat exchangers (for cooling) following each reactor. By way of example, U.S. Patent Application Publication No. 2014/0107385 to Schammel et al. describes a system that uses a series of catalytic beds where the inlet temperature is less than 600° C. All of the catalytic beds are kept at the same temperature throughout the reaction process by removing thermal energy generated during the upstream reactions. While this system can help with the energy input requirements needed for the OCM reaction, it relies on additional materials and a complicated catalytic bed design, which can be expensive and difficult to implement on a commercial scale. Moreover, the methane conversion within each reactor must be limited to avoid runaway reaction and excessive catalyst temperature.

SUMMARY OF THE INVENTION

A solution to the aforementioned problems associated with the OCM reaction has been discovered. Embodiments of the invention utilizes parameters of the feed reactant gas to establish and maintain reaction conditions in the OCM reactor so that the conversion of methane to ethane and/or ethylene is maximized while the destruction of the catalyst by excessive temperatures in the reactor is avoided. In particular, in embodiments of the invention, the OCM reaction is ignited in a manner that avoids transient state at temperatures that would destroy the catalyst. Once in an ignited state, the reaction is made to operate in an autothermal state by supplying feed gas for the oxidative coupling reaction to the reactor at a rate and at a low enough temperature to compensate for the heat of reaction generated in the reactor. In this way, the feed gas serves as a coolant as it is heated to a higher temperature by the heat generated by the oxidative coupling reaction in the reactor.

In embodiments of the invention, the reactor is operated as an adiabatic reactor with a particular combination of operating parameters (e.g., feed composition, feed temperature, feed flowrate, or combinations thereof) so that the reactor is in an ignited, autothermal state. In the autothermal state, the reactor feed is controlled at a very high flowrate and low temperature thus providing the cooling for removing the large heat of reaction and enabling high methane conversion (for example >15%) within a single reactor.

In one instance of the present invention, a method of performing an oxidative coupling of methane reaction to produce $C_2+$ hydrocarbons is described. The method can include pre-heating a gaseous feed stream, which has an initial methane to oxygen ($CH_4:O_2$) molar ratio, to a temperature of at least 400° C. (e.g., 400° C. to 750° C., or 550° C. to 650° C.). The preheated gaseous feed stream can be introduced into an adiabatic reactor that includes a catalyst bed containing an oxidative coupling of methane catalyst. The oxidative coupling of methane reaction can be ignited. During the startup procedures, both the temperature and the $CH_4:O_2$ molar ratio of the gaseous feed stream introduced into the adiabatic reactor can be incrementally reduced to a temperature of 10° C. to 350° C. and a final $CH_4:O_2$ molar ratio of 9:1 to 3:1 such that the sum of the gaseous feed stream temperature and the rise in temperature within the reactor over the start-up period (e.g., 1 minute to 5 hours) is close to the desired operating temperature (e.g., 750° C. to 1100° C. or 850° C. to 950° C.) of the reaction. By "close," it is meant that the temperature at the exit of the reactor is within 15%, or within 5% of the final operating temperature. The initial $CH_4:O_2$ molar ratio can be 8:1 to 40:1 and the final $CH_4:O_2$ molar ratio can be 9:1 to 3:1, 8:1 to 5:1, or 6:1 to 5:1, preferably 5.5:1, after incremental reduction. The method can further include adding 1 mole % to 10 mole % of a gas more reactive than methane to the gaseous feed stream prior to ignition, and discontinuing the addition after ignition. In some instances, the gaseous feed stream can have a residence time of 0.1 to 20 milliseconds in the catalyst bed after ignition. In certain embodiments, the gaseous feed stream can have a residence time of 25 to 1000 milliseconds in the catalyst bed before and during ignition, and the method further includes decreasing the residence time to 0.1 to 20 milliseconds after ignition. The preferred residence time depends on the activity of the catalyst.

In another aspect of the present invention, there is disclosed a startup process for an OCM reaction that can include: (a) pre-heating a catalyst bed of an adiabatic reactor with a heat source; (b) introducing a gaseous feed stream comprising methane ($CH_4$) and oxygen ($O_2$) having a temperature of less than 350° C. and an initial $CH_4:O_2$ molar ratio to the adiabatic reactor; (c) igniting the oxidative coupling of methane reaction; and (d) incrementally reducing, during startup steps (a) to (c), the initial $CH_4:O_2$ molar ratio of the gaseous feed stream introduced into the reactor to a final $CH_4:O_2$ molar ratio of 9:1 to 3:1. The catalyst bed can include an oxidative coupling of methane catalyst. The temperature of the gaseous feed stream introduced into the reactor can be 150° C. or less and the catalyst bed can be preheated to 400° C. to 700° C., preferably 550° C. to 650° C., more preferably 500° C. to 600° C. In certain embodiments, the catalyst bed can be preheated to the ignition temperature of the oxidative coupling of methane reaction at the initial $CH_4:O_2$ molar ratio and the catalyst bed will ignite shortly after the feed mixture is introduced. (The ignition conditions may be found experimentally.)

After startup procedures have been performed and a steady reaction state has been reached (e.g., usually within 1 minute to 5 hours after startup, depending on the thermal capacitance of the reactor and insulation), a product stream can be produced that includes $C_2+$ hydrocarbons with a selectivity to $C_2+$ hydrocarbons of 30% to 95%. This can be achieved with using a reactant feed having a temperature of less than 150° C., preferably 75° C. to 125° C., or about 100° C. (i.e., ambient temperature). In some instances, the product stream also includes hydrogen ($H_2$) and carbon monoxide (CO), carbon dioxide ($CO_2$), or mixtures thereof.

The OCM catalyst used in the methods of the present invention can be any catalyst known in the art. (However, the minimum feed temperature possible depends on the catalyst activity.) In certain embodiments, the catalyst can include a metal oxide, a supported metal oxide, a mixed metal oxide, a supported mixed metal oxide, or any mixture thereof. In a particular instance, the catalyst can be $La_2O_3/CeO_2$, $SrO/La_2O_3$, $Yb_2O_3$—$SrO$—$CeO_2$, $Li/MgO$, $Na_2WO_4$—$Mn$—$O/SiO_2$, or any combination thereof.

In one aspect of the present invention, 20 embodiments are described. Embodiment 1 is a method of performing an oxidative coupling of methane reaction to produce $C_2+$ hydrocarbons, the method comprising: (a) preheating a gaseous feed stream to a temperature of at least 400° C., wherein the gaseous feed stream comprises methane ($CH_4$) and oxygen ($O_2$) having an initial $CH_4:O_2$ molar ratio; (b) introducing the preheated gaseous feed stream to an adiabatic reactor, wherein the adiabatic reactor includes a catalyst bed comprising an oxidative coupling of methane catalyst; (c) igniting the oxidative coupling of methane reaction; and (d) after igniting the oxidative coupling of methane reaction, incrementally reducing both the temperature and the $CH_4:O_2$ molar ratio of the gaseous feed stream introduced into the adiabatic reactor to an operating temperature of 10° C. to 350° C. and a final $CH_4:O_2$ molar ratio of 9:1 to 3:1 over a startup period such that, at the operating temperature, the oxidative coupling of methane reaction remains ignited and the reactor is in an autothermal state. Embodiment 2 is the method of embodiment 1, wherein the initial $CH_4:O_2$ molar ratio is 8:1 to 40:1 and the final $CH_4:O_2$ molar ratio is 9:1 to 3:1, 8:1 to 5:1, or 6:1 to 5:1, preferably 5.5:1 after incremental reduction. Embodiment 3 is the method of embodiment 2, wherein the temperature is reduced in 1 to 10° C. increments and the molar ratio is reduced in 0.01 to 1 molar increments. Embodiment 4 is the method of any one of embodiments 1 to 3, wherein a final catalyst operating temperature is 750° C. to 1100° C. or 850° C. to 950° C. Embodiment 5 is the method of any one of embodiments 1 to 4, wherein the gaseous feed stream is preheated to 400° C. to 750° C., or 500° C. to 600° C. Embodiment 6 is the method of any one of embodiments 1 to 5, further comprising: adding 1 mol % to 10 mol % of a gas more reactive than methane to the gaseous feed stream prior to ignition; and discontinuing the addition after ignition. Embodiment 7 is the method of any one of embodiments 1 to 6, wherein the gaseous feed stream has a residence time of 0.1 to 1000 milliseconds in the catalyst bed before and during ignition, and the method further comprises decreasing the residence time to 0.1 to 20 milliseconds after ignition. Embodiment 8 is the method of any one of embodiments 1 to 7, further comprising continuing the oxidative coupling of methane reaction after step (d) to produce a product stream comprising $C_2+$ hydrocarbons. Embodiment 9 is the method of embodiment 8, wherein the product stream further comprises hydrogen ($H_2$) and carbon monoxide (CO), carbon dioxide ($CO_2$), water ($H_2O$) or mixtures thereof. Embodiment 10 is the method of any one of embodiments 1 to 9, wherein the catalyst comprises a metal oxide, a supported metal oxide, a mixed metal oxide, a supported mixed metal oxide, or any mixture thereof. Embodiment 11 is the method of embodiment 10, wherein the catalyst is $La_2O_3/CeO_2$, $SrO/La_2O_3$, $Yb_2O_3$—$SrO$—$CeO_2$, $Li/MgO$, $Na_2WO_4$—$Mn$—$O/SiO_2$, or any combination thereof. Embodiment 12 is the method of any one of embodiments 1 to 11, wherein the selectivity of $C_2+$ hydrocarbons is 30% to 95% after ignition.

Embodiment 13 is a startup method for an oxidative coupling of methane reaction to produce $C_2+$ hydrocarbons, the method comprising: (a) preheating a catalyst bed of an adiabatic reactor with a heat source, wherein the catalyst bed comprises an oxidative coupling of methane catalyst; (b) introducing a gaseous feed stream comprising methane ($CH_4$) and oxygen ($O_2$) having a temperature of less than 350° C. and an initial $CH_4:O_2$ molar ratio to the adiabatic reactor; (c) igniting the oxidative coupling of methane reaction; and (d) incrementally reducing the initial $CH_4:O_2$ molar ratio of the gaseous feed stream introduced into the reactor to a final $CH_4:O_2$ molar ratio of 9:1 to 3:1 over steps (a) through (c). Embodiment 14 is the method of embodiment 13, wherein the initial $CH_4:O_2$ molar ratio is 5:1 to 40:1 and the final $CH_4:O_2$ molar ratio is 9:1 to 3:1, 8:1 to 5:1, or 6:1 to 5:1, preferably 5.5:1 after incremental reduction. Embodiment 15 is the method of embodiment 13, wherein the temperature of the gaseous feed stream introduced into the reactor is 150° C. or less and the catalyst bed is preheated to 400° C. to 700° C., preferably 500° C. to 600° C. Embodiment 16 is the method of embodiment 13, wherein the catalyst bed is preheated to at least the ignition temperature of the oxidative coupling of methane reaction at the initial $CH_4:O_2$ molar ratio and the reactor is in an ignited condition. Embodiment 17 is the method of embodiment 16, wherein ignited conditions comprise a Zeldovich number (B) of greater than or equal to four and the product of a Damköhler number (Da) and Zeldovich number (B×Da) of greater than or equal to one. Embodiment 18 is the method of any one of embodiments 13 to 17, wherein the heat source is removed in any one of steps (a)-(d) after the catalyst bed has been preheated. Embodiment 19 is the method of any one of embodiments 13 to 18, wherein of the characteristic heat removal (heat loss) time from the adiabatic reactor is higher than the residence time required to achieve substantially complete conversion of the oxygen. Embodiment 20 is the method of any one of embodiments 13 to 19, continuing the oxidative coupling of methane reaction after step (d) to produce a product stream comprising $C_2+$ hydrocarbons.

The following includes definitions of various terms and phrases used throughout this specification.

The phrase "ambient temperature" when used in the context of a reactant feed during steady state operation of an OCM reaction means a temperature of 40° C. or less, preferably less than 30° C.

The phrase "steady state" refers to a reactor system where the parameters of the reactor system are a constant or substantially constant value. Steady state parameters of the system include reactant feed temperature, pressure, feed composition including $CH_4:O_2$ mole ratio, feed flow rate, methane and oxygen conversion, product composition, and catalyst bed temperature.

The terms "about" or "approximately" are defined as being close to as understood by one of ordinary skill in the art. In one non-limiting embodiment the terms are defined to be within 10%, preferably within 5%, more preferably within 1%, and most preferably within 0.5%.

The term "$C_x+$ hydrocarbons" where x is an integer refers to a mixture of hydrocarbons having a carbon number of x and more. For example $C_2+$ hydrocarbons is a mixture of hydrocarbons having 2 and more carbon numbers.

The term "substantially" and its variations are defined as being largely but not necessarily wholly what is specified as understood by one of ordinary skill in the art. In one non-limiting embodiment, substantially refers to ranges within 10%, within 5%, within 1%, or within 0.5%.

The terms "wt. %", "vol. %", mol. % refers to a weight, volume, or molar percentage of a component, respectively, based on the total weight, the total volume, or total moles of material that includes the component. In a non-limiting example, 10 grams of component in 100 grams of the material is 10 wt. % of component.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with any of the terms "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The methods of the present invention can "comprise," "consist essentially of," or "consist of" particular ingredients, components, compositions, etc., disclosed throughout the specification. With respect to the transitional phase "consisting essentially of," in one non-limiting aspect, a basic and novel characteristic of the methods of the present invention is the ability to provide the gaseous feed stream to the reactor at ambient temperature during steady state operation of an OCM reaction.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description.

BRIEF DESCRIPTION OF THE DRAWINGS

FIG. 2A includes a single gaseous feed stream and FIG. 2B includes two gaseous feed stream inlets.

Figure 1A:
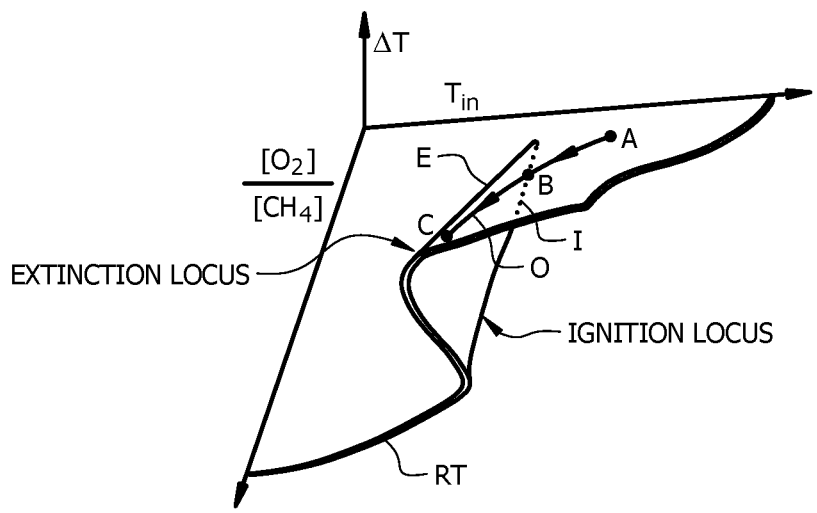
FIG. 1A shows a schematic representation of an oxidative coupling of methane steady state reactor exit temperature as a function of feed temperature, and oxygen to methane feed ratio.

While the invention is susceptible to various modifications and alternative forms, specific embodiments thereof are shown by way of example in the drawings and may herein be described in detail. The drawings may not be to scale.

DETAILED DESCRIPTION OF THE INVENTION

Embodiments of the invention involve the use of parameters of the feed gas to an oxidative coupling of methane reactor to establish and maintain the oxidative coupling of methane reaction in the reactor. For example, the OCM reaction is ignited in a manner that avoids transient state at temperatures that would destroy the catalyst. Once the OCM reaction is in an ignited state, the feed gas may be used as a coolant so that the reactor may be operated in an autothermal and ignited state. In the autothermal state, the oxidative coupling of methane reaction uses only the heat produced by the reaction itself. In other words, in the autothermal state, no external heating is provided to carry out the oxidative coupling reaction at steady state. In the ignited state, the catalyst is above its ignition temperature. The catalyst reaches its ignition temperature when the catalyst heats up to a point so that no external heating is required. At the ignition temperature, the rate of heat generation exceeds the rate of heat removal (by the flow). The reaction is ignited successfully when the catalyst is at, or above, its ignition temperature, but below temperatures at which the catalyst is destroyed and when the OCM reaction is occurring.

As mentioned previously, the oxidative coupling reaction is so exothermic that the temperature in the reactor may far exceed the ignition temperature of the catalyst and reach a temperature that destroys (deactivates) the catalyst. Such high temperatures often occur in a transient state. Hence, embodiments of the invention may also include an innovative start-up procedure that enables the attainment of an autothermal and ignited state while avoiding a transient state in which the temperatures may be high enough to destroy the catalyst. The start-up procedure may best be understood by considering how the various parameters interact with each other to create reaction conditions in the oxidative coupling of methane reactor.

Figure 1B:
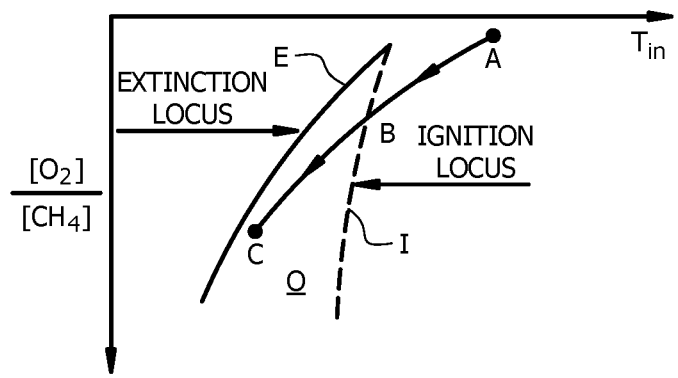
FIG. 1B shows a schematic of the projection of the ignition and extinction locus in the plane of oxygen to methane ratio and feed gas temperature.
Figure 1C:
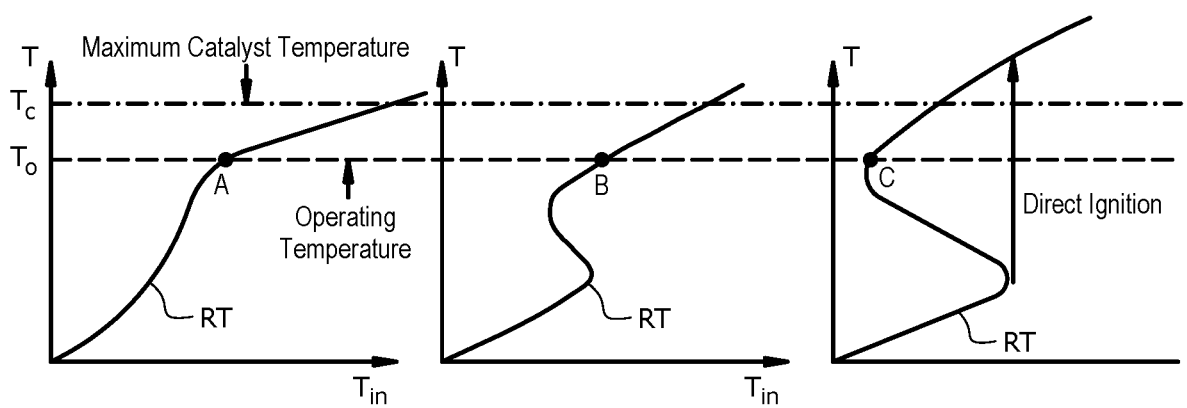
FIG. 1C shows another schematic representation of an oxidative coupling of methane steady state reactor exit temperature as a function of feed temperature, and oxygen to methane feed ratio.

FIGS. 1A to 1C show a range of operating parameters in which both an ignited and an extinguished state coexist for the OCM reaction and the region of steady-state multiplicity. FIG. 1A is a three-dimensional graph showing the difference between the reactor exit and feed temperatures ($\Delta T$) on the y-axis, temperature of the inlet feed ($T_{in}$) on the x-axis and the ratio of $O_2/CH_4$ in the reactor on the z-axis. FIG. 1B is a top plan view of FIG. 1A, which shows $T_{in}$ on the x-axis in relation to the ratio $O_2/CH_4$ on the z-axis. FIG. 1C is a cross-sectional view of FIG. 1A at successively higher values of $O_2/CH_4$ ratio, which shows $\Delta T$ on the y-axis in relation to the $T_{in}$ on the x-axis. The path labeled A-B-C shows one example of a preferred start-up path going from initial (extinguished) state A to a final ignited operating state C.

In embodiments of the invention, the special start-up procedure may be followed to enable attainment of a stable ignited state, while avoiding the problem of transient heating of the catalyst to temperatures sufficient to decompose the catalyst or significantly reduce the catalyst activity. In embodiments of the invention, this start-up procedure involves simultaneously changing more than one control variable to enable the system to move along a special path from an initial state to a final ignited operating state, namely from state A, to state C, via state B, as shown in FIGS. 1A to 1C. This ultimately can allow for the use of a reactant feed at substantially reduced temperatures compared to the adiabatic temperature for a given feed ratio (for example a feed temperature 600-900° C. lower than the adiabatic temperature). The feed temperature at point C is less than that at point B, which is less than at point A.

Referring to FIGS. 1A and 1B, line E represents the extinction locus of the catalyst and line I represents the ignition locus of the catalyst. The catalyst is extinguished when it is no longer able to maintain autothermal operation and the oxygen conversion is very low (e.g., <20%). The catalyst is ignited when it reaches a temperature at which the activity is high enough to maintain autothermal operation with high oxygen conversion (e.g., >80%).

Starting from some low value of $T_{in}$ (anywhere to the left of line E) in FIG. 1B, ignition occurs when the feed temperature is increased enough to cross line I, the ignition locus, while moving from left to right. Once the reactor is in the ignited state, reducing $T_{in}$ causes a gradual reduction in reactor (catalyst) temperature until line E is crossed (moving from right to left); at which point the reaction extinguishes and there is an abrupt decrease in catalyst and reactor temperature.

Considering FIG. 1A, once in the ignited state, the region to the right of line I remains in that state. The region "O," enclosed by the ignition and extinction loci (denoted by curves I and E in FIG. 1B), is the region of viable performance in the reactor for the oxidative coupling reaction to produce ethane and/or ethylene. Within this region, operation close to the extinction locus is optimal.

In embodiments of the invention, the oxidative coupling reaction process is designed to take place at state C in region O. Further, in embodiments of the invention the reaction is carried out at steady state at state C, having moved the reaction conditions from startup condition A outside of region O, proceeding to intermediate state B and then finally to state C.

Referring to FIGS. 1A and 1C, line RT represents a plot of reactor exit temperature (T) versus inlet feed temperature $T_{in}$. Line $T_c$ shows the maximum operating temperature of the catalyst and line $T_o$ shows the operating temperature of the reactor. Temperatures at and above $T_c$ will destroy or deactivate the catalyst. For example, if the temperature of the catalyst exceeds 700° C., the catalyst might evaporate or change its oxidation state. For pelletized catalysts, the thermal stress at such a high temperature may cause the pellets to fracture, disintegrate and get blown out of the reactor.

In embodiments of the invention, the oxidative coupling reaction is carried out in region O, preferably at or near state C to achieve favorable conditions for conversion to ethane and/or ethylene without destroying the catalyst by excessive heat. To get to state C, embodiments of the invention start at point A (highest inlet feed temperature ($T_o$), and lowest ratio $O_2/CH_4$—relative to points B and C). The reaction conditions are changed to proceed along line A-B-C to reach point B (approximately equal exit temperature, lower inlet feed temperature ($T_o$), and higher ratio $O_2/CH_4$—relative to point A). The reaction conditions are further changed to proceed along line A-B-C to reach point C (approximately equal exit temperature, lowest inlet feed temperature ($T_o$), and highest ratio $O_2/CH_4$—relative to points A and B). Developing the reaction conditions in this way along line A-B-C, as illustrated, the reactor attains an autothermal state while avoiding a transient state in which the catalyst is exposed to high transient temperatures, which could potentially extinguish the catalyst. Once the reaction conditions are at state C, the feed to the reactor is at a low enough temperature to provide a high cooling rate while still enabling operation in the autothermal state.

Thus, the present application provides for an OCM startup process that can result in the use of a gaseous feed stream (e.g., $CH_4$ and $O_2$) at ambient or near ambient temperatures after the initial startup phase has been completed and the reaction has reached steady state operating conditions. The startup process can be used with any known OCM catalyst. The startup procedure involves igniting the reaction and then changing at least one operating parameter to obtain desired steady state conditions and using near ambient reactant feed temperatures to keep the reaction in an auto-thermal state. In embodiments of the invention, such as some embodiments where a portion of the feed gas is recycled from a cryogenic separation tower, the temperature may be well below ambient temperature for example much below 30° C. In such embodiments, the feed gas rate may be reduced as less feed gas would be required to cool the reactor and maintain it in an auto-thermal state.

In embodiments of the invention, the startup procedure involves starting at a high temperature feed (at state A, FIG. 1) and varying any combination of the following parameters: (1) ratio of $O_2/CH_4$, (2) temperature of feed, (3) residence time in the reactor, and (4) initial temperature of the catalyst.

By implementing the startup procedure and implementing a low temperature feed as described herein, embodiments of the invention provides advantages such as: (1) reducing capital costs associated with large heat exchangers needed to pre-heat the feed gas to high temperatures for ignition; (2) use of an economical adiabatic reactor instead of a cooled multi-tubular reactor or a more complex fluidized bed reactor; (3) operation with higher methane conversion than is possible with a cooled multi-tubular or fluidized bed reactor; and (4) stable operation at the highest possible throughput or production rate leading to a smaller reactor.

These and other non-limiting aspects of the present invention are discussed in further detail in the following sections.

A. Oxidative Coupling of Methane Process

Figure 2A:
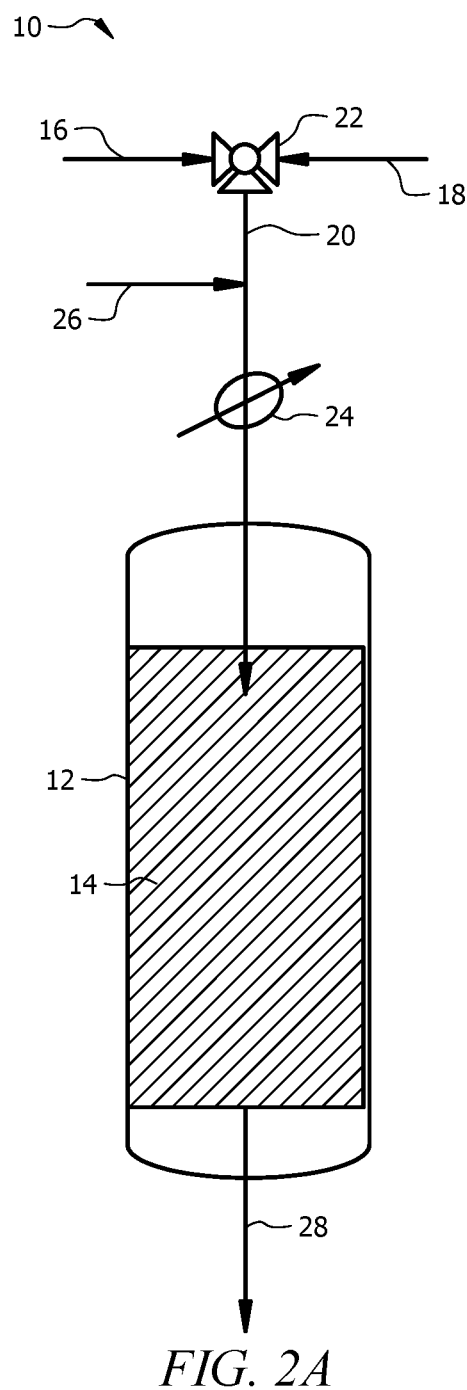
FIGS. 2A and 2B are a schematic of embodiments of a system to produce $C_2+$ hydrocarbons using the method of the present invention.
Figure 2B:
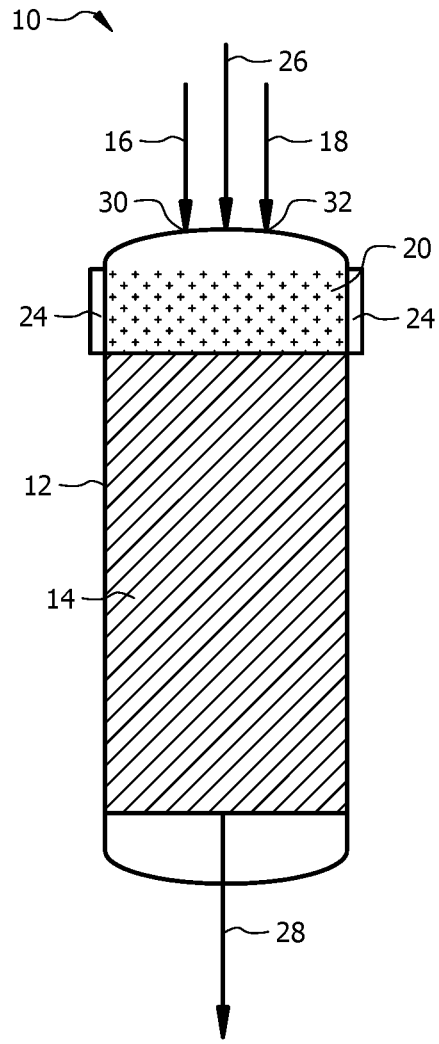

In an OCM reaction, a gaseous feed mixture containing methane ($CH_4$) and oxygen ($O_2$) can be contacted with an OCM catalyst under suitable conditions to produce a product stream that includes $C_2$+ hydrocarbons. The $C_2$+ hydrocarbons are obtained from oxidative coupling of $CH_4$. FIG. 2A is a schematic of a reactor system for an OCM process having a single gaseous feed mixture. Referring to FIG. 2, a schematic of system 10 for the production of ethylene is depicted. System 10 may include an adiabatic reactor 12 and a catalytic bed 14 that includes catalytic material capable of catalyzing an oxidative coupling of methane reaction. Gaseous methane stream 16 and gaseous oxygen source stream 18 can be combined to produce gaseous feed stream 20. Flow controller 22 can be used to control the amount of methane and/or oxygen fed to reactor 12. As shown, flow controller 22 is a three-way valve, however, any type of flow controller (e.g., mass flow meter) or valve configuration or series of flow controllers or valves can be used to control the flow of the oxygen source and methane source to reactor 12. In some embodiments, the methane source and the oxygen source are fed as individual gas feeds to reactor 12, and form the gaseous feed mixture 20 in reactor 12. Referring to FIG. 2B, methane feed stream can enter reactor 12 through inlet 30. Oxygen source feed stream 18 can enter reactor 12 through inlet 32. Inlets 30 and 32 can include necessary valves or meters to control the flow and/or amount of gas enter the reactor 12 for both methane feed stream 16 and oxygen source feed stream 18. The reactor 12 can include other conventional components for controlling chemical reactions such as, for example, heating elements, thermocouples, manual and/or automated controllers, valves, and the like. Average operating pressure of reactor 12 can be about 0.1 MPa, with other ranges contemplated 0.1 to 0.2 MPa, preferably between 0.2 and 1.0 MPa.

The following subsections provide non-limiting startup procedures for initiating an OCM reaction. In addition to being able to use a reactant feed at or near ambient temperatures during steady state operation, these startup procedures can advantageously limit excessive heat production. Wishing not to be bound by theory, it is believed that limiting excessive heat production can result in lower carbon dioxide and/or carbon monoxide formation during the OCM reaction, thereby increasing $C_2$+ selectivity.

1. Incremental Change of $CH_4:O_2$ Molar Ratio and Feed Temperature

The startup of the reactor of the present invention can be controlled such that the sum of the gaseous feed stream temperature and a rise of a temperature of the reactor over a startup period is close to a final catalyst operating temperature of the reaction. Such control allows the reaction to be performed in adiabatic reactors instead of cooled multi-tubular reactors or fluidized bed reactors. During startup, gaseous feed stream 20 can have an initial $CH_4:O_2$ molar ratio of 5:1 to 40:1, or 8:1 to 40:1, or 10:1 to 40:1, or 15:1 to 35:1, or 20:1 to 30:1, or any range or value there between (e.g., 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1). In some embodiments, gaseous feed stream 20 or the individual streams (streams 16 or 18) that make up the gaseous feed stream can be at a temperature considered to be below or at ambient temperatures of an OCM process prior to entering reactor 12. By way of example, gaseous feed stream 20 can be made up of recycled streams from a cryogenic separation process. In some embodiments, gaseous feed stream 20 can have a temperature of less than 400° C.

Referring to FIG. 2A, gaseous feed stream 20 can be heated by passing the stream through preheater 24 to heat the stream to a temperature of at least 400° C., or 400° C. to 750° C., or 550° C. to 650° C., or 500° C. to 600° C., or any value or range there between (e.g., 400° C., 425° C., 450° C., 475° C., 500° C., 525° C., 550° C., 575° C., 600° C., 625° C., 650° C., 675° C., 700° C., or 725° C., 750° C.). As the preheated feed passes over the catalyst bed, ignition of the catalyst can occur and the oxidative reaction commences (See reaction equations (V) through (VIII)). In some embodiments, gas stream 26, which is more reactive than methane, can be added to gaseous feed stream 20 prior to reaction ignition. After ignition, flow of gas stream 26 can be slowed or discontinued by adjusting a flow controller associated with the reactive gas stream. Non-limiting examples of gases more reactive (with oxygen) than methane include hydrogen, ethane, ethylene, propane, propylene, diazomethane, tributylborane, and triethylborane. At this stage of the OCM startup process, the reactor 12 and/or the catalytic bed 14 is not heated. In other instances, however, the reactor 12 and/or catalytic bed 14 can be heated.

Upon ignition of the oxidative coupling of methane reaction, the product stream 28, which includes the $C_2$+ hydrocarbons, is produced. At this time, both the temperature and the $CH_4:O_2$ molar ratio of the gaseous feed stream introduced into the adiabatic reactor can be reduced to a temperature of 10° C. to 350° C. and a final $CH_4:O_2$ molar ratio of 9:1 to 3:1. The temperature of gaseous feed stream 20 can be reduced in 1 to 10° C. increments by reducing the heat provided by preheater 24. For example, preheater 24 can be turned off or down to allow the temperature of the gaseous feed stream to decrease in 1° C., 5° C., 10° C., 20° C. increments, or increments of 1° C., 2° C., 3° C., 4° C., 5° C., 6° C., 7° C., 8° C., 9° C., 10° C., 15° C., 20° C., etc. In some embodiments, cooling can be used to control the reduction of the gaseous feed stream. Preheater 24 can be a furnace, heat exchanger, heater, electrical heater, steam or the like. The final catalyst operating temperature, after the initial startup procedures have been performed, can be 750° C. to 1100° C. or 850° C. to 950° C., or 750° C., 760° C., 770° C., 780° C., 790° C., 800° C., 810° C., 820° C., 830° C., 840° C., 850° C., 860° C., 870° C., 880° C., 890° C., 900° C., 910° C., 920° C., 930° C., 940° C., 950° C., 960° C., 970° C., 980° C., 990° C., 1000° C., 1010° C., 1020° C., 1030° C., 1040° C., 1050° C., 1060° C., 1070° C., 1080° C., 1090° C., 1100° C. Using flow controller 22 of FIG. 2A, or flow controllers in inlets 30 and 32 of FIG. 2B, the flow of oxygen and methane to reactor 12 can be adjusted to change the $CH_4:O_2$ molar ratio in the gaseous feed stream entering reactor 12 in 0.01 to 1 molar increments (e.g., 0.01, 0.02, 0.05, 1, 1.5, 2, etc., increments), while maintaining a desired flow rate. The final $CH_4:O_2$ molar ratio can be 9:1 to 3:1, 8:1 to 5:1, or 6:1 to 5:1, preferably 5.5:1 after incremental reduction. The incremental reduction rate of the gaseous feed stream temperature and the $CH_4:O_2$ molar ratio can be correlated to the rise of the temperature of the adiabatic reactor over the startup period (e.g., 1 minute to 5 hours) and of the final catalyst operating temperature, as shown in the following equation (IX).

$$T_f + \Delta T_{ad} = T_{out} \quad (IX)$$

where $T_f$ is the gaseous reactant feed temperature entering the reactor 12, $\Delta T_{ad}$ is the adiabatic temperature rise of the reactor 12, and Tout is the final catalyst or catalyst bed operating temperature at the exit of the catalyst bed. $\Delta T_{ad}$ is directly proportional to the oxygen concentration in the feed (or equivalently the $O_2$ to $CH_4$ molar ratio).

2. Incremental Change of Residence Time

In combination with the parameters described above, the rate of the gaseous feed stream can be controlled to provide a first residence time (e.g., 0.1 to 1000 milliseconds, or 50 to 900 milliseconds, 100 to 800 milliseconds, 200 to 700 milliseconds, etc.) in the catalyst bed before and during ignition. Once ignition has commenced, the flow of the gaseous feed stream can be adjusted to afford a smaller residence time (e.g., 20 to 0.1 milliseconds, 15 to 1 milliseconds, or 10 to 2 milliseconds) in the catalyst bed as compared to the first residence time.

3. Incremental Change of $CH_4:O_2$ Molar Ratio at "Ignition" Conditions

In some embodiments, the startup procedure can include preheating the catalyst bed to a temperature near or above the ignition conditions. By preheating the catalyst bed, the gaseous feed stream can be introduced at a lower temperature but still sufficient for ignition of the catalyst bed into the auto-thermal state while avoiding uncontrolled runaway of the reaction. Uncontrolled runway conditions are conditions in which the temperature within the catalyst bed is so high as to damage the catalyst.

The proper ignition conditions can be determined using a combination of a Zeldovich number (B) and a Damköhler number (Da). The Zeldovich and Damköhler numbers are dimensionless groups. Zeldovich number is the non-dimensional adiabatic temperature rise given by, $B = [(-\Delta H) \cdot Y_{O2} / C_p] \times [E/RT^2]$; where $\Delta H$ is the overall heat (or enthalpy change) of reaction, $Y_{O2}$ is the mole fraction of oxygen in the reactant mixture, $C_p$ is the molar heat capacity of the reactant mixture, E is the activation energy of the reaction, R is the gas constant, and T is the absolute feed temperature. The Damköhler number is the non-dimensional residence time given by, $Da = k(T) \cdot \tau$; where $k(T)$ is the overall (first order) rate constant for the reaction evaluated at the feed temperature and $\tau$ is the residence time in the catalyst bed evaluated at the feed temperature.

There are two conditions necessary for operation in the autothermal (or ignited) state. First, steady state multiplicity must be possible for some combinations of the control variables; the condition for this is BA. Second, the reactor must be started up in a manner such that the condition for ignition is exceeded; the product of Damköhler number (Da) and Zeldovich number (B×Da) is greater than or equal to one. (BDa≥1) is the condition for ignition in an adiabatic reactor.

Processes according to embodiments of the invention can include introducing gaseous feed stream 20 with an initial $CH_4:O_2$ molar ratio at as low a residence time as possible to catalyst bed 14. The catalyst bed 14 can be preheated to an ignition temperature. By way of example, catalyst bed 14 can be preheated to 400° C. to 700° C., preferably 550° C. to 650° C., or 400° C., 410° C., 420° C., 430° C., 440° C., 450° C., 460° C., 470° C., 480° C., 490° C., 500° C., 510° C., 520° C., 530° C., 540° C., 550° C., 560° C., 570° C., 580° C., 590° C., 600° C., 610° C., 620° C., 630° C., 640° C., 650° C., 660° C., 670° C., 680° C., 690° C., 700° C. The residence time of gaseous feed stream 20 in catalyst bed 14 can be 0.1 to 20 milliseconds, 1 to 15 milliseconds, or 2 to 10 milliseconds, or 0.1, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20. Gaseous feed stream 20 can have a temperature of less than 350° C., less than 150° C., or 15 to 350° C., or 100 to 300° C., 125 to 250° C. The feed stream 20 does not have to be subjected to any additional heating prior to entering reactor 12 (e.g., preheater 24 does not have to be used). As gaseous feed stream 20 enters heated catalyst bed 14, the OCM reaction can ignite. After ignition of the OCM reaction, the initial $CH_4:O_2$ molar ratio of gaseous feed stream 20 can be incrementally reduced to a final $CH_4:O_2$ molar ratio of 9:1 to 3:1 (e.g., 8:1 to 5:1, or 6:1 to 5:1, preferably 5.5:1) by adjusting the methane content and oxygen content in the gaseous feed stream (e.g., adjusting the flow of gaseous methane stream 16 and/or oxygen feed stream 18 using valve 22). In some embodiments, after catalyst bed 14 has been preheated, the heating can be turned down or off during introduction of gaseous feed stream 20 and/or ignition of the OCM reaction. In certain embodiments, the heat generated is sufficient to maintain or increase the temperature of the catalyst bed.

4. Continued Production of $C_2$+ Hydrocarbons

In the methods described above, after startup is complete (e.g., when the reaction reaches steady state conditions) the OCM reaction is continued by maintaining the reaction in an autothermal state using gaseous methane stream 16 as a coolant while product stream 26 is continued to be produced. Steady state conditions can include a constant reaction temperature (e.g., the reaction temperature does not vary by more than 10% from a selected reaction temperature—by way of example, a selected reaction temperature of 850° C. can include a temperature range 765° C. to 935° C.). Product stream 26 can exit adiabatic reactor 12 and be collected, stored, transported, or processed into other chemical products. By way of example, product stream 26 that includes $C_2+$ hydrocarbons and water produced from the reaction can be collected in a collection device and/or transported via piping to a separation unit. In the separation unit, the $C_2+$ hydrocarbons can be separated using known separation techniques, for example, distillation, absorption, membrane technology, etc., to produce an ethylene containing product. In embodiments when carbon dioxide is in the reactant mixture and/or generated in situ, the resulting gases (for example, CO, $H_2$, and ethylene) produced from the systems of the invention (for example, system 10) is separated from the hydrogen, carbon monoxide, and carbon dioxide (if present) using known separation techniques, for example, a hydrogen selective membrane, a carbon monoxide selective membrane, a carbon dioxide selective membrane, or cryogenic distillation to produce one or more products such as ethylene, carbon monoxide, carbon dioxide, hydrogen, or mixtures thereof. The products can be used in additional downstream reaction schemes to create additional products or for energy production. Examples of other products include chemical products such as methanol production, olefin synthesis (e.g., via Fischer-Tropsch reaction), aromatics production, carbonylation of methanol, carbonylation of olefins, the reduction of iron oxide in steel production, etc. The method can further include isolating and/or storing the produced gaseous mixture or the separated products.

B. Catalytic Material and Reactants

One or more OCM catalysts can be used in the process of the present invention. The catalyst(s) can be a supported catalyst(s), a bulk metal catalyst(s), or an unsupported catalyst(s). The support can be active or inactive. The catalyst support can include MgO, $Al_2O_3$, $SiO_2$, or the like. All of the support materials can be purchased or be made by processes known to those of ordinary skill in the art (e.g., precipitation/co-precipitation, sol-gel, templates/surface derivatized metal oxides synthesis, solid-state synthesis, of mixed metal oxides, microemulsion technique, solvothermal, sonochemical, combustion synthesis, etc.). One or more of the catalysts can include one or more metals or metal compounds thereof. Non-limiting catalytic metals include Li, Na, Ca, Cs, Mg, La, Ce, W, Mn, Ru, Rh, Ni, or Pt, or combinations or alloys thereof. Non-limiting examples of catalysts of the invention include: (1) La on a MgO support; (2) Na, Mn, and $La_2O_3$ on an aluminum support; (3) Na and Mn oxides on a silicon dioxide support; (4) $Na_2WO_4$ and Mn on a silicon dioxide support, or any combination thereof. Non-limiting examples of some particular catalysts that can be used in the context of the present invention to promote oxidative coupling of methane to produce ethylene are $Li_2O$, $Na_2O$, $Cs_2O$, MgO, $WO_3$, $Mn_3O_4$, $La_2O_3/CeO_2$, $SrO/La_2O_3$, $Yb_2O_3$—SrO—$CeO_2$, Li/MgO, $Na_2WO_4$—Mn—$O/SiO_2$, or any combination thereof.

The gaseous feeds stream in the context of the present invention can be a gaseous mixture that includes, but is not limited to, a hydrocarbon or mixtures of hydrocarbons and oxygen. The hydrocarbon or mixtures of hydrocarbons can include natural gas, liquefied petroleum gas containing of $C_2$-$C_5$ hydrocarbons, $C_6+$ heavy hydrocarbons (e.g., $C_6$ to $C_{24}$ hydrocarbons such as diesel fuel, jet fuel, gasoline, tars, kerosene, etc.), oxygenated hydrocarbons, and/or biodiesel, alcohols, or dimethyl ether. In a preferred aspect, the hydrocarbon is a mixture of hydrocarbons that is predominately methane (e.g., natural gas). The oxygen containing gas used in the present invention can be air, oxygen enriched air, oxygen gas, and can be obtained from various sources. The reactant mixture may further contain other gases, provided that these do not negatively affect the reaction. Examples of such other gases include carbon dioxide, nitrogen, and/or hydrogen. The hydrogen may be from various sources, including streams coming from other chemical processes, like ethane cracking, methanol synthesis, or conversion of methane to aromatics. Carbon dioxide may be from natural gas, or a waste or recycle gas stream (e.g., from a plant on the same site, like for example from ammonia synthesis) or after recovering the carbon dioxide from a gas stream.

EXAMPLES

The present invention will be described in greater detail by way of specific examples. The following examples are offered for illustrative purposes only, and are not intended to limit the invention in any manner.

Example 1

Figure 3:
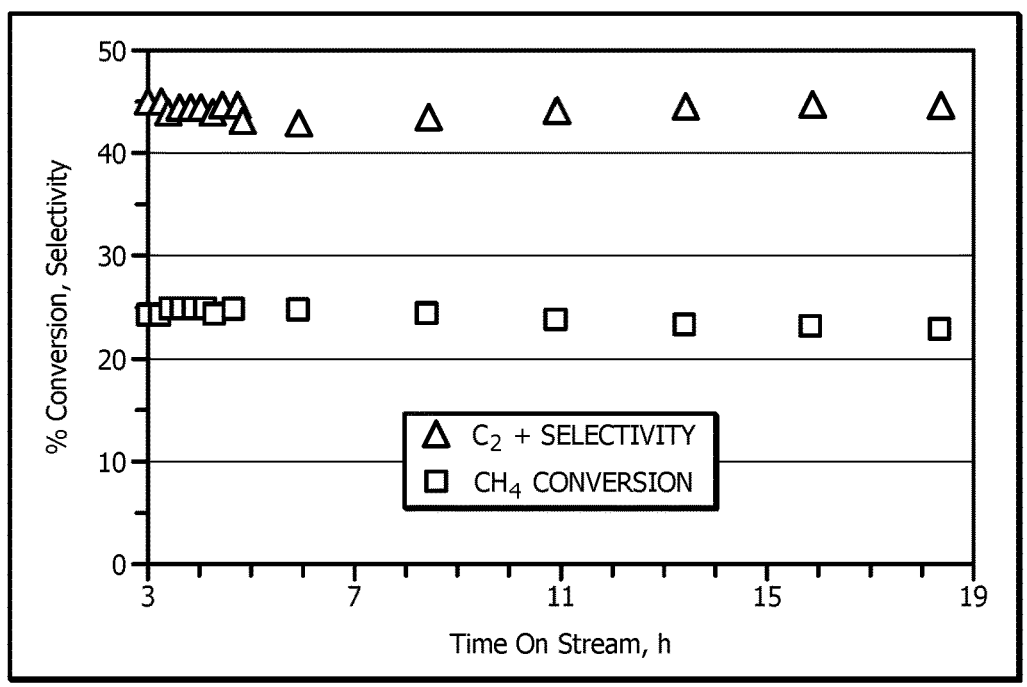
FIG. 3 is graphical representation of $CH_4$ conversion and $C_2+$ selectivity of a $La_2O_3/CeO_2$ catalyst driven OCM reaction, with a La/Ce weight ratio of about 15, a feed molar $CH_4$:$O_2$ of 4, a residence time of about 7 milliseconds, and a feed temperature of near ambient.

Incremental Change of $CH_4$:$O_2$ Molar Ratio and Feed Temperature with a $La_2O_3/CeO_2$ Catalyst A 10.5 mm I.D. quartz reactor was used as the adiabatic reactor. A gaseous feed mixture that included reactant gases $CH_4$ and $O_2$ at a $CH_4$:$O_2$ molar ratio of 20:1 was introduced to the adiabatic reactor. The gaseous mixture was preheated to about 550-600° C. and had a residence time of from about 0.1 milliseconds to about 100 milliseconds in the catalyst bed that included a $La_2O_3/CeO_2$ catalyst having a La/Ce wt. ratio of 15. The feed composition and feed temperature during start up were changed in small steps simultaneously to a final $CH_4$:$O_2$ molar ratio of 4 to 5, and to an ambient feed temperature (e.g., less than 20° C.). The outlet gas from the reactor was determined by GC analysis to include $C_2$ and higher hydrocarbons and syngas composition, such as $C_2H_4$, $C_2H_6$, $CH_4$, CO, $H_2$, $CO_2$ and $H_2O$. A steady performance for the duration of experiment (about 20 hours) was achieved. The selectivity to $C_2$ and higher hydrocarbons was comparable or better than that of conditions of the comparative examples discussed in Example 2. FIG. 3 shows the performance ($CH_4$ and $C_2+$ selectivity of $La_2O_3/CeO_2$ catalyst at a final $CH_4$:$O_2$ molar ratio, residence time of about 7 milliseconds; and a feed temperature equal to near ambient temperature.

Example 2

Comparative Example of Example 1—No Change in Startup Procedures

As a comparative example, an experiment performed with the same catalyst and reactor with the final conditions of Example 1 being used as the start-up and final conditions. Negligible methane conversion (<1%) was observed.

Example 3

Comparative Example of Example 1—Change in Temperature

As a comparative example, an experiment performed with the same catalyst and reactor and at same final conditions of Example 1 was performed, except that only one parameter i.e., temperature was varied by keeping feed ratio constant at 4 and residence time of 7 milliseconds. The reaction was sustained when the feed temperature was reduced to about 160° C., but quickly died upon reducing the temperature to ambient. 'Residence time' refers to the contact time of the flowing gases (at reaction conditions) in the catalyst bed and is defined as the ratio of void volume in the catalyst bed to the actual volumetric flow rate under reactive conditions.

Comparison of Example 1 to Comparative Examples 2 and 3 demonstrated that varying two parameters during startup (i.e., change in molar ratio and feed temperature) provided a desired steady state condition and conversion of methane instead of little to no conversion of methane (Example 2) when the reaction was started at the desired operating conditions and/or extinction of the catalyst as demonstrated in Example 3 when only the temperature was changed during startup.

Example 4

Incremental Change of $CH_4:O_2$ Molar Ratio, Feed Temperature and Residence Time with a $Na_2WO_4$—Mn—$O/SiO_2$ Catalyst A 22 mm I.D. quartz tube was used as the reactor. A gaseous feed mixture that included reactant gases $CH_4$ and $O_2$ at a $CH_4:O_2$ molar ratio of about 16 was introduced to the reactor. The gaseous mixture was preheated to about 650-700° C. and had a residence time of from about 25 milliseconds to about 200 milliseconds in the catalyst bed that included a $Na_2WO_4$—Mn—$O/SiO_2$ catalyst. The feed composition and feed temperature during start up were changed in small steps simultaneously to a final $CH_4:O_2$ molar ratio of 4 to 5, and a temperature of about 100° C. The residence time was lowered to about 40 milliseconds when the temperature was about 400° C. and the $CH_4:O_2$ molar ratio was about 5. The outlet gas from the reactor was determined by GC analysis to include $C_2$ and higher hydrocarbons and syngas composition, such as $C_2H_4$, $C_2H_6$, $CH_4$, CO, $H_2$, $CO_2$, and $H_2O$. A steady performance for the duration of the experiment was achieved at a final reactor feed temperature of 110° C., a final $CH_4:O_2$ molar ratio of about 3.5, and a residence time of 40 milliseconds. The performance of the $Na_2WO_4$—Mn—$O/SiO_2$ catalyst under these reaction conditions are presented in Table 1. The percent methane conversion was 27%.

TABLE 1

| $C_2$+ Selectivity | |
|---|---|
| % Ethylene | 25.43 |
| % Ethane | 9.33 |
| % Propene | 2.62 |
| % Propane | 0.3 |
| % total $C_2$+ | 37.68 |
| % CO | 32.92 |
| % $CO_2$ | 29.39 |
| % $H_2$/CO | 0.82 |
| Ethylene/ethane | 2.73 |

Example 5

Comparative Example of Example 4—No Change in Startup Procedures

As a comparative example, an experiment performed with the same catalyst and reactor and at same final conditions of Example 4 was performed, but without preheating the catalyst or feed gas to sufficiently high temperature to achieve the ignited state. Negligible methane conversion (<1%) was observed, because only the extinguished state was reached.

Comparison of Example 4 to Comparative Example 5 demonstrated that varying two parameters during startup (i.e., change in molar ratio and feed temperature) provided a desired steady state condition and conversion of methane instead of little to no conversion of methane (Example 2) when the reaction was started at the desired operating condition.

Example 6

Incremental Change of $CH_4:O_2$ Molar Ratio, Feed Temperature with a $Yb_2O_3$—SrO—$CeO_2$ Catalyst A 22 mm I.D. quartz tube was used as the reactor. A gaseous feed mixture that included reactant gases $CH_4$ and $O_2$ at a $CH_4:O_2$ molar ratio of about 20 was introduced to the reactor. The gaseous mixture was preheated to about 600° C. and had a residence time of from about 0.5 milliseconds to about 5 milliseconds in the catalyst bed that included a $Yb_2O_3$SrO—$CeO_2$ catalyst. The feed composition and feed temperature during start up were changed in small steps simultaneously to a final $CH_4:O_2$ molar ratio of about 5, and a temperature of about 130° C. The outlet gas from the reactor was determined by GC analysis to include $C_2$ and higher hydrocarbons and syngas composition, such as $C_2H_4$, $C_2H_6$, $CH_4$, CO, $H_2$, $CO_2$, and $H_2O$. A steady performance for the duration of the experiment was achieved at a final feed temperature of 130° C., a final $CH_4:O_2$ molar ratio of about 4.7, and a residence time of 4 milliseconds. The performance of the $Yb_2O_3$—SrO—$CeO_2$ catalyst under these reaction conditions are presented in Table 2. The percent methane conversion was 11.53%.

TABLE 2

| $C_2$+ Selectivity | |
|---|---|
| % Ethylene | 21.19 |
| % Ethane | 14.22 |
| % Propene | 0.77 |
| % Propane | 0.41 |
| % total $C_2$+ | 36.58 |
| % CO | 13.18 |
| % $CO_2$ | 50.24 |
| % $H_2$/CO | 2.32 |
| Ethylene/ethane | 1.49 |

Example 7

Comparative Example of Example 6—No Change in Startup Procedures

As a comparative example, an experiment performed with the same catalyst and reactor and at final conditions of Example 6 without following the preferred path. Only an extinguished final state was reached with negligible methane conversion (<1%).

Comparison of Example 6 to Comparative Example 7 demonstrated that varying two parameters during startup (i.e., change in molar ratio and feed temperature) provided a desired steady state condition and conversion of methane instead of little to no conversion of methane (Example 2) when the reaction was started at the desired operating condition.

Example 8

Effect of Reactor Size

Figure 4:
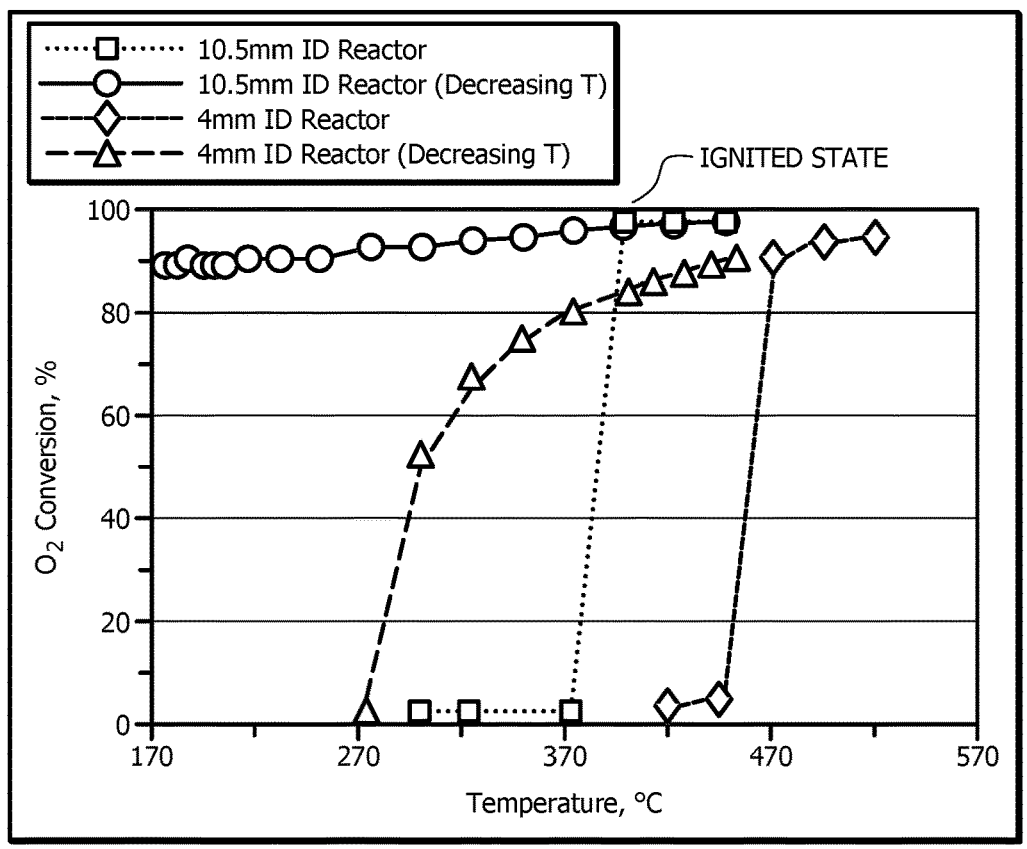
FIG. 4 is graphical representation of ignition and extinction of a $La_2O_3/CeO_2$ catalyst driven OCM reaction, with a La/Ce weight ratio of about 15, in a 4 mm and a 10.5 mm I.D. reactor.

The effect of reactor size on heat removal was investigated using 4 mm and 10.5 I.D. reactor tubes by changing only the furnace temperature (i.e., all other parameters were kept constant). The reaction parameters were a $CH_4:O_2$ molar ratio of about 4 and a residence time of about 2 milliseconds. A La—Ce catalyst having a La/Ce weight ratio of 15 was used. FIG. 4 shows ignition and extinction of the La—Ce oxide catalyst for the 4 mm and 10.5 mm I.D. reactors, respectively. It was observed when a larger reactor size was used, the characteristic heat removal time was much larger and the extinction temperature was lowered further. From the data obtained from the 10.5 mm reaction (FIG. 4) it was determined that the extinction temperature was lower than 160° C. as compared to about 270° C. for the smaller reactor. When the furnace was opened in the larger reactor to further reduce the temperature close to ambient, the reactor extinguished. Also, the ignition temperature was about 400° C., which was lower than the ignition temperature of 475° C. observed in the smaller reactor.

The invention claimed is:

1. A startup method for an oxidative coupling of methane reaction to produce $C_2+$ hydrocarbons, the method comprising the steps of:
    (a) preheating a catalyst bed of an adiabatic reactor with a heat source, wherein the catalyst bed comprises an oxidative coupling of methane catalyst;
    (b) introducing a gaseous feed stream comprising methane ($CH_4$) and oxygen ($O_2$) having a temperature of less than 350° C. and an initial $CH_4:O_2$ molar ratio to the adiabatic reactor;
    (c) igniting the oxidative coupling of methane reaction; and
    (d) incrementally reducing the initial $CH_4:O_2$ molar ratio of the gaseous feed stream introduced into the reactor to a final $CH_4:O_2$ molar ratio of 9:1 to 3:1 over steps (a) through (c).

2. The method of claim 1, wherein the initial $CH_4:O_2$ molar ratio is 5:1 to 40:1 and the final $CH_4:O_2$ molar ratio is 9:1 to 3:1 after incremental reduction.

3. The method of claim 1, wherein the temperature of the gaseous feed stream introduced into the reactor is 150° C. or less and the catalyst bed is preheated to 400° C. to 700° C.

4. The method of claim 1, wherein the catalyst bed is preheated to at least the ignition temperature of the oxidative coupling of methane reaction at the initial $CH_4:O_2$ molar ratio and wherein the reactor is in an ignited condition.

5. The method of claim 4, wherein ignited conditions comprise a Zeldovich number (B) of greater than or equal to four and the product of a Damköhler number (Da) and Zeldovich number (B×Da) of greater than or equal to one.

6. The method of claim 1, wherein the heat source is removed in any one of steps (a)-(d) after the catalyst bed has been preheated.

7. The method of claim 1, wherein of the characteristic heat removal time from the adiabatic reactor is higher than the residence time required to achieve substantially complete conversion of the oxygen.

8. The method of claim 1, further comprising continuing the oxidative coupling of methane reaction after step (d) to produce a product stream comprising $C_2+$ hydrocarbons.

* * * * *